(12) United States Patent
Tsuji et al.

(10) Patent No.: US 8,349,608 B2
(45) Date of Patent: Jan. 8, 2013

(54) METHOD FOR PRODUCTION OF TOOTH, AND TOOTH PRODUCED BY THE METHOD

(75) Inventors: Takashi Tsuji, Nagareyama (JP); Nobuo Sakuragawa, Sagamihara (JP)

(73) Assignees: Organ Technologies Inc., Tokyo (JP); The Kitasato Gakuen Foundation, Tokyo (JP); Nidek Co., Ltd., Gamagoori (JP)

( * ) Notice: Subject to any disclaimer, the term of this patent is extended or adjusted under 35 U.S.C. 154(b) by 279 days.

(21) Appl. No.: 12/528,936

(22) PCT Filed: Feb. 28, 2008

(86) PCT No.: PCT/JP2008/053529
§ 371 (c)(1),
(2), (4) Date: Jan. 4, 2010

(87) PCT Pub. No.: WO2008/105499
PCT Pub. Date: Sep. 4, 2008

(65) Prior Publication Data
US 2010/0129771 A1    May 27, 2010

(30) Foreign Application Priority Data
Feb. 28, 2007    (JP) ................. 2007-049128

(51) Int. Cl.
C12N 5/00    (2006.01)
C12N 5/02    (2006.01)
(52) U.S. Cl. ........................... 435/377; 435/325
(58) Field of Classification Search ............. 435/377, 435/325
See application file for complete search history.

(56) References Cited

U.S. PATENT DOCUMENTS

| | | | |
|---|---|---|---|
| 5,885,829 A * | 3/1999 | Mooney et al. | 435/325 |
| 2003/0235580 A1 * | 12/2003 | Zhang | 424/130.1 |
| 2005/0089513 A1 | 4/2005 | Sakuragawa et al. | |
| 2007/0207127 A1 | 9/2007 | Kato et al. | |
| 2007/0231275 A1 | 10/2007 | Ueda | |
| 2008/0039940 A1 | 2/2008 | Hashimoto et al. | |

FOREIGN PATENT DOCUMENTS

| | | |
|---|---|---|
| EP | 1 259 593 B1 | 4/2005 |
| EP | 1 690 929 A1 | 8/2006 |
| EP | 1 731 177 A | 12/2006 |
| EP | 1 905 459 A1 | 4/2008 |
| EP | 1 914 300 A1 | 4/2008 |
| JP | A-2004-254682 | 9/2004 |
| JP | A-2004-331557 | 11/2004 |
| JP | A-2004-357567 | 12/2004 |
| JP | A-2006-59 | 1/2006 |
| JP | A-2006-6249 | 1/2006 |
| WO | WO 2004/018658 A1 | 3/2004 |
| WO | WO 2005/035739 A1 | 4/2005 |
| WO | WO 2005/087286 A1 | 9/2005 |
| WO | WO 2006/019357 A1 | 2/2006 |
| WO | WO 2006/129672 A1 | 12/2006 |

OTHER PUBLICATIONS

Risbud et al., "Stem cells in craniofacial and dental tissue engineering," Orthod Craniofacial Res, 2005, pp. 54-59, vol. 8, Blackwell Munksgaard.
Shi et al., "The efficacy of mesenchymal stem cells to regenerate and repair dental structures," Orthod Craniofacial Res, 2005, pp. 191-199, vol., 8, Blackwell Munksgaard.
Ohazama et al., "Stem-cell based Tissue Engineering of Murine Teeth," J Dent Res, 2004, pp. 518-522, vol. 83, No. 7.
Miki et al., "Stem Cell Characteristics of Amniotic Epithelial Cells," Stem Cells, 2005. pp. 1549-1559, vol. 23.
De Coppi et al., "Isolation of amniotic stem cell lines with potential for therapy," Nature Biotechnology, Jan. 2007, pp. 100-106, vol. 25, No. 1.
Fukuchi et al., "Human Placenta-Derived Cells Have Mesenchymal Stem/Progenitor Cell Potential," Stem Cells, 2004, pp. 649-658, vol. 22.
Kim et al., "Human amniotic fluid-derived stem cells have characteristics of multipotent stem cells," Cell Proliferation, 2007, pp. 75-90, vol. 40, Blackwell Publishing Ltd.
Supplementary European Search Report and Annex for European patent Application No. 08712100.0, mailed on Mar. 10, 2010.
Young et al., "Tissue Engineering of Complex Tooth Structures on Biodegradable Polymer Scaffolds," J Dent Res, 2002, pp. 695-700, vol. 81, No. 10.
Nakao et al., "The development of a bioengineered organ germ method," Nature Methods, Mar. 2007, pp. 227-230, vol. 4, No. 3, Nature Publishing Group. (w/5 pp. of Supplementary Notes).
Kobayashi et al., "HLA Expression Analysis of Human Amniotic Side Population (SP) Cells and Isolation of Mesenchymal Stem Cell-like Cells from the Same," Reprod Immunol Biol, 2006, p. S46, vol. 21, No. 2. (w/English translation).
Sakuragawa et l., "Human Amnion Mesenchyme Cells Express Phenotypes of Neuroglial Progenitor Cells," Journal of Neuroscience Research 2004, pp. 208-214, vol. 78.
International Search Report for International Application No. PCT/JP2008/053529, issued on Apr. 15, 2008, pp. 1-3, ISA: Japanese Patent Office. Office Action with English-language translation issued in Russian Patent Application No. 2009135689/15, mailed Nov. 17, 2011
Notice of Reasons for Rejection dated Apr. 10, 2012 for Japanese Patent Application No. 2007-049128 (with translation).
Australian Office Action dated Oct. 15, 2012 from Australian Patent Application No. 2008219982.

* cited by examiner

Primary Examiner — Marcia S Noble
(74) Attorney, Agent, or Firm — Oliff & Berridge, PLC

(57) ABSTRACT

Disclosed is a method for producing a tooth, which comprises the steps of: positioning a first cell mass substantially comprising either one of amniotic mesenchymal cells or epithelial cells, and a second cell mass substantially comprising the other one in the inside of a support carrier while keeping them in close contact with each other without being mixed together; and culturing the first and second cell masses in the inside of the support carrier.

12 Claims, 2 Drawing Sheets

METHOD FOR PRODUCTION OF TOOTH, AND TOOTH PRODUCED BY THE METHOD

TECHNICAL FIELD

The present invention relates to a method for producing a tooth, and a tooth obtained thereby.

BACKGROUND ART

A tooth is an organ having enamel in the outermost layer and dentin in its inner layer, both of which are hard tissues; an odontoblast, which produces the dentin, inside the dentin; and dental pulp in the central portion. Teeth may be lost by dental caries, periodontal diseases or the like, and from the viewpoint of the significant influence of the presence or absence of teeth on appearance and taste of food, and from the viewpoint of maintaining health and a high quality of life, various tooth regenerative techniques have been developed.

For example, in *J. Dent. Res.*, 2002, Vol. 81(10), pp. 695-700, it is disclosed that a tooth-like tissue is regenerated by transplanting cells, such as epithelial cells isolated from a tooth germ and mesenchymal dental follicle cells, with a biodegradative carrier into an abdominal cavity of a rat.

As a method of regenerating a tooth germ, it is described, for example, in Japanese Patent Application Laid-open (JP-A) No. 2004-331557, that tooth germ cells isolated from a living body are cultured in the presence of biologically active substances such as fibroblast growth factors and the like. In JP-A No. 2004-357567, it is proposed that at least one type of cells selected from tooth germ cells and cells which can be differentiated into these tooth germ cells, both of them are isolated from a living body, are cultured along with a fibrin-containing carrier, and it is described that a "tooth" having a specific shape is formed by using a fibrin-containing carrier having the desired shape for the tooth germ.

On the other hand, from the viewpoint of regenerative medicine, recent interest has focused on reuse of biological samples which had been hitherto discarded. Especially, unlike tissues excised due to diseases, recent interest has focused on tissues such as umbilical cord and amnion, which had been discarded at delivery, as organs having stem cells and capable of being involved in cell differentiation.

Examples of the techniques which focus attention on amnion include JP-A 2006-6249 which discloses a technique in which epithelial cells and interstitial cells derived from amnion are grown in a large amount in an undifferentiated state. It describes that cells grown by this method are useful in regenerative medicine and the like since they have multipotency similar to that of undifferentiated embryonic stem cells.

JP A 2004-254682 describes that side population cells were isolated from the human amniotic mesenchymal cell layer and human amniotic epithelial cell layer as stem cells. It describes that the side population cells are at least capable of differentiating into nerve cells and useful as the source of substances produced by nerve cells.

DISCLOSURE OF THE INVENTION

However, in order for a regenerated tooth or a tooth germ to function as a tissue, it is indispensable that multiple types of cells constituting the tissue be positioned (cell arrangement) at appropriate relative positions. It is difficult to provide a tooth that is effective as a tissue simply by using amnion.

Accordingly, the object of the present invention is to provide a new use of amnion as well as to provide a method for producing a tooth with which a tooth having the specific cell arrangement is produced.

The present invention was made in view of the above-described circumstances, and provides a method for producing a tooth and a tooth obtained by using the method.

The first aspect of the present invention provides a method for producing a tooth, the method including:

positioning, in a support carrier, a first cell mass substantially consisting of only either one of amnion-derived mesenchymal cells or epithelial cells and a second cell mass substantially consisting of only the other one of the mesenchymal cells or epithelial cells, the first and second cell masses not being mixed with each other but made to closely contact each other; and culturing the first and second cell masses in the support carrier.

The second aspect of the present invention provides a tooth obtained by the above-described production method.

According to the present invention, a new use of amnion may be provided, and a tooth having a specific cell arrangement may be provided.

BEST MODE FOR CARRYING OUT THE INVENTION

Figure 1A:
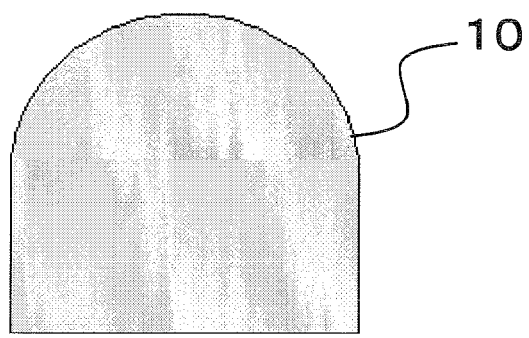
FIG. 1A is a schematic conceptual views showing the procedure according to Examples of the present invention for reconstruction of a tooth germ using mesenchymal cells and epithelial cells derived from a tooth germ, and showing the state of a gel drop before cell arrangement.

The method of the present invention for producing a tooth includes:

positioning, in a support carrier, a first cell mass substantially consisting of only either one of amnion-derived mesenchymal cells or epithelial cells, and a second cell mass substantially consisting of only the other one of the mesenchymal cells or epithelial cells, the first and second cell masses not being mixed with each other but made to closely contact each other (hereinafter referred to as "positioning step"); and culturing the first and second cell masses in the support carrier (hereinafter referred to as "culturing step").

In the above-described production method, the amnion is preferably derived from the amniotic compact layer.

In the above-described production method, the epithelial cells are preferably derived from at least one of a tooth germ, skin, mucosa or gingiva, and more preferably derived from a tooth germ.

In the above-described production method, the first cell mass or second cell mass substantially comprising the amnion-derived mesenchymal cells is preferably a cell mass composed of single cells, and the first cell mass and second cell mass are more preferably both composed of single cells.

Since, in the present production method, cell masses formed from each of amnion-derived mesenchymal cells and epithelial cells are positioned in a support carrier so as to contact with each other without being mixed with each other, and cultured, the cell arrangement specific to a tooth, that is, dentin inside and enamel outside, may be effectively reproduced, forming a tooth as a tissue.

Further, by using amnion, especially amnion-derived mesenchymal cells, which has/have often been discarded, as a material for producing a tooth, a new candidate for a material for a tooth may be created, and a new mode of usage of amnion may be provided.

In the present invention, the term "tooth" means a tissue continuously having a layer of dentin inside and a layer of enamel outside, preferably a tissue having directionality resulting from a crown and a root. The directionality of a tooth may be identified by arrangement of its crown and root. The crown and root may be visually confirmed based on their shapes, histological staining or the like. The crown means a part having a layer structure of enamel and dentin, and the enamel layer is absent in the root.

Dentin and enamel may be easily and morphologically identified by those skilled in the art by histological staining or the like. Enamel may also be identified by the presence of an ameloblast, which may be confirmed by the presence/absence of amelogenin. On the other hand, dentin may be identified by the presence of an odontoblast, which may be confirmed by the presence/absence of dentin sialoprotein. Confirmation of amelogenin and dentin sialoprotein may be carried out easily by a method well-known in the art, and examples of the method include in situ hybridization and staining with an antibody, or the like.

The directionality of a tooth may be identified by the arrangement of its crown and root. The crown and root may be visually confirmed based on their shapes, histological staining or the like.

In the present invention, the terms "tooth germ" and "tooth bud" are used to refer specifically to those distinguished based on the developmental stages described later. In this case, "tooth germ" means an early embryo of a tooth, which is destined to become a tooth in the future, and which is at a stage including the bud stage and the bell stage according to typical developmental staging of a tooth, and especially means such a tissue in which no accumulation of dentin and enamel is observed, which are characteristic to the hard tissue of a tooth. On the other hand, "tooth bud" means a tissue at a stage between the transitional stage from "tooth germ" used in the present invention, that is, the stage where the accumulation of dentin and enamel characteristic to the hard tissue of a tooth starts, and the stage before a tooth germinates from gingiva to exert typical functions of a tooth.

Development of a tooth from a tooth germ follows each of the bud stage, the cap stage, the early bell stage and the late bell stage. Here, at the bud stage, epithelial cells invaginate such that they wrap around mesenchymal cells, and when reaching the early bell stage and the late bell stage, the epithelial cell portion becomes the outer enamel and the mesenchymal cell portion begins to form dentin internally. Therefore, a tooth is formed from a tooth germ by cell-cell interaction between epithelial cells and mesenchymal cells.

In the present invention, "mesenchymal cell" means a cell derived from a mesenchymal tissue and "epithelial cell" means a cell derived from an epithelial tissue.

Further, in the present invention, "periodontal tissue" means alveolar bone and periodontal membrane formed mainly in the outer layer of a tooth. Alveolar bone and periodontal membrane may be morphologically and easily identified by those skilled in the art by histological staining or the like.

The method for preparing tooth of the present invention will now be described.

In the positioning step of the method for preparing tooth of the present invention, the first cell mass and the second cell mass are brought into contact with each other and positioned in the support carrier.

Here, each of the first cell mass and the second cell mass is substantially composed of only the mesenchymal cells or only the epithelial cells. The cell mass substantially composed of only the mesenchymal cells contains the above-mentioned mesenchymal cells for the formation of a tooth. The cell mass containing the mesenchymal cells for formation of a tooth may be prepared by a preparation step according to the above-mentioned production method, and, on the other hand, the cell mass substantially composed of only the epithelial cells may be prepared independently from the cell mass substantially composed of only the mesenchymal cells (a first cell preparation step and a second cell preparation step).

The term "cell mass" means a state in which cells are closely packed, and the cells may be either in the state of a tissue or in the state of single cells. The term "substantially consist(s) of" means that the amount of matters included other than the cells of interest is as small as possible. In the present invention, the cell mass substantially consisting of amniotic mesenchymal cells is composed of single cells, whereas the cell mass substantially consisting of epithelial cells may be either a part of a tissue or a mass of single cells. It is preferred that both the epithelial cells and mesenchymal cells be cell masses composed of single cells since multiple teeth may be formed simultaneously after culturing.

One of the first cell mass or the second cell mass may be epithelial cells or mesenchymal cells. The numbers of cells constituting these cell masses vary depending on the species of the animal and on the type, hardness and size of the support carrier, and may be generally from $10^1$ to $10^8$ cells, and preferably from $10^3$ to $10^8$ cells per cell mass.

The mesenchymal cells used in the present invention are amnion-derived mesenchymal cells. Amnion is an organ which constitutes a part of placenta and which wraps a fetus in uterus, and it is usually discarded as excrement at delivery. In the present invention, the means of acquisition of the amnion is not restricted as long as amnion may be obtained thereby, but amnion as a waste at delivery is preferably used.

Amnion is composed of three layers, that is, the amniotic epithelial cell layer and the amniotic basement membrane layer, and the amniotic compact layer which is thicker than these layers. The amnion-derived mesenchymal cells in the present invention may be mesenchymal cells derived from the amniotic compact layer among these.

The amnion-derived mesenchymal cells may be individually selected from the whole amnion tissue using the surface antigen pattern or the like, but they are preferably prepared from the amniotic compact layer after separation thereof from the amniotic epithelial cell layer since this can reduce contamination of other cells.

Separation of the amniotic compact layer from the other cell layers may be carried out either by physical separation using scissors or the like from the other cell layers based on the thickness and morphology of the membrane, or by chemical separation using enzyme treatment from the epithelial cell layer or the basement membrane layer. The enzyme used to obtain the compact layer may be one capable of separating the epithelial cell layer, and examples thereof preferably used include trypsin for separation of the epithelial layer and dispase for digestion of the basement membrane layer. These enzymes may be used either individually or in combination. The cell layer obtained after removing the epithelial cell layer and the basement membrane layer by these enzyme treatments may be used as the amniotic compact layer.

The processing temperature and processing time for the enzyme treatment, as well as the conditions for centrifugation and stirring that are optionally employed, may be appropriately selected depending on the enzyme activities of the enzymes used, and those skilled in the art may easily carry out desired enzyme treatments. These enzyme treatments may be repeated or carried out using a combination of multiple types of enzymes depending on the condition of the tissue. The treatment with the enzyme(s) may be carried out by referring to a known literature, for example, J. Neurosci. Res. 78, 208-214, 2004.

In cases where the amniotic mesenchymal cells were obtained as the amniotic compact layer, the amniotic compact layer may further be made into single cells by an enzyme treatment, agitation or the like. Examples of the enzyme(s) which may be used to make the amniotic compact layer into single cells include collagenase, dispase and papain. These enzymes may be used either individually or in combination. The concentrations and treatment conditions for these enzymes may be easily and appropriately selected by those skilled in the art.

The cell mass substantially consisting of the mesenchymal cells may contain, as long as amnion-derived mesenchymal cells are included therein, other mesenchymal cells.

Examples of the mesenchymal cells other than the above mesenchymal cells may include mesenchymal cells derived from a tooth germ and from other than a tooth germ. Examples of the mesenchymal cells derived from other than a tooth germ include cells derived from other mesenchymal tissues in a living body, such as, preferably, bone marrow cells not containing blood cells and mesenchymal stem cells, more preferably, mesenchymal cells in the oral cavity, bone marrow cells inside the jawbone, mesenchymal cells derived from cranial neural crest cells, mesenchymal precursor cells which can generate the mesenchymal cells, and stem cells thereof.

In cases where mesenchymal cells other than those derived from amnion are used as the mesenchymal cells, the amount of the amnion-derived mesenchymal cells is preferably at least not less than 50% by mass, more preferably not less than about 75% by mass, still more preferably not less than about 90% by mass to surely obtain a tooth having a desired cell arrangement, although the amount varies depending on the origin and tooth-forming potential of the other mesenchymal cells. The amount of not less than 50% by mass is preferred since a desired tooth may be surely obtained irrespective of the level of the tooth-forming potential of the mesenchymal cells derived from the other tissue.

The epithelial cells used in the present invention are preferably derived from a tooth germ so that they may reproduce the cell arrangement in a living body and effectively form a tooth having a specific structure and directionality, and preferably at a stage between the bud stage and the cap stage from the viewpoints of immaturity and homogeneity of the differentiation stage of the cells.

The epithelial cells may also be those derived from other than a tooth germ, and examples thereof include cells derived from other epithelial tissues in a living body. Preferred examples of the epithelial cells include epithelial cells of skin, mucosa and gingiva in the oral cavity, and more preferred examples of the epithelial cells include immature epithelial precursor cells which can produce differentiated, for example, keratinized or parakeratinized, epithelial cells such as skin, mucosa and the like. Examples of such immature epithelial precursor cells include non-keratinized epithelial cells and stem cells thereof.

In cases where cells are isolated from tissues for preparation of a cell mass, a tooth germ and other tissues may be collected from the jawbone or the like of various animals, for example, primates such as humans and monkeys and ungulates such as pigs, cows and horses, which are mammals; and rodents such as mice, rats and rabbits, which are small mammals. For the collection of the tooth germ and the tissue, a condition generally used for collecting a tissue may be applied without modification, and the tooth germ and the tissue may be collected under sterile conditions and stored in an appropriate preservation solution. Examples of a human tooth germ include the tooth germ of a third molar, which is the so-called wisdom tooth, as well as a fetal tooth germ, and, from the viewpoint of utilization of autogenous tissues, usage of the tooth germ of a wisdom tooth is preferred.

In cases where the above cells are prepared from a tissue, for example, a tooth germ, the tooth germ isolated from its surrounding tissue is first divided into a tooth germ mesenchymal tissue and a tooth germ epithelial tissue based on their shapes. Since the tooth germ tissue can be structurally identified under the microscope, it can be easily isolated by tearing or cutting using dissecting scissors, forceps or the like. Isolation of the tooth germ mesenchymal tissue and the tooth germ epithelial tissue from the tooth germ can be easily carried out based on their shapes, by tearing or cutting using injection needles, tungsten needles, forceps or the like.

Preferably, an enzyme may be used to easily isolate the tooth germ cells from their surrounding tissue and/or to isolate an epithelial tissue and a mesenchymal tissue from the tooth germ tissue. Examples of the enzyme used in such applications include dispase, collagenase and trypsin.

The cells constituting the cell masses may be prepared from the state of a collected tissue into the state of single cells. In the preparation step, an enzyme may be used to make the cells easily dispersible as single cells. Examples of such an enzyme include dispase, collagenase and trypsin. In this case, for the isolation of epithelial cells from an epithelial tissue, it is preferred to perform trypsin treatment and DNase treatment after collagenase treatment. On the other hand, for the isolation of mesenchymal cells from a mesenchymal tissue, it is preferred to perform collagenase treatment and trypsin treatment simultaneously and to finally perform DNase treatment. In this case, the DNase treatment is performed in order to prevent a decrease in the amount of recovered cells due to cell aggregation caused by DNA released into the solution when a part of the cells are damaged by the enzyme treatment and the cell membrane is lysed.

The cells constituting the cell masses may be those which have been subjected to preliminary culture prior to the positioning step in order to obtain a sufficient number of each kind of the cells. For the cell culture, a condition, such as temperature, generally used for culture of animal cells may be applied without modification.

As the medium used for the culture, a medium generally used for animal cell culture, such as Dulbecco's Modified Eagle Medium (DMEM), may be used, and serum for promotion of cell proliferation may be added, or, as an alternative to the serum, a cellular growth factor such as FGF, EGF or PDGF or a known serum component such as transferrin may be added. In cases where serum is added, its concentration may be changed appropriately depending on the culture conditions, and may usually be 10% by volume. For the cell culture, normal culture conditions, such as those for culture in an incubator at 37° C. under 5% $CO_2$, may be applied. An antibiotic such as streptomycin may be added as appropriate.

With regard to positioning of the cell masses in the positioning step, the first and second cell masses are positioned in the support carrier which can maintain the contacting state of the cells. In this case, the cell masses do not mix with each other. Thus, since the cell masses are positioned without being mixed with each other, a boundary surface is formed between the cell masses. Such a mode of positioning is called "compartmentalization" as appropriate in the present specification.

The support carrier used herein may be one in which cells may be cultured, and is preferably a mixture with the above-described medium. Examples of such a support carrier include collagen, fibrin, laminin, extracellular matrix mixture, polyglycolic acid (PGA), polylactic acid (PLA), lactic acid/glycolic acid copolymer (PLGA), Cellmatrix (trade name), Mebiol Gel (trade name) and Matrigel (trade name). These support carriers may have a hardness with which the cells can be virtually maintained at the locations where they were positioned in the support carrier, and examples of these support carriers include those in the forms of a gel, fiber and solid. In this case, the hardness with which the cells can be virtually maintained at their locations may be hardness which is applicable to three-dimensional culture, that is, a hardness with which the position of the cells can be maintained while hypertrophy of the cells due to their proliferation is not inhibited, and such hardness can be easily determined. For example, in the case of collagen, usage at the final concentration of 2 to 3 mg/ml provides an appropriate hardness.

Further, in this case, the support carrier may have a thickness sufficient for allowing growth of the first and second cell masses inside the carrier, and the thickness may be appropriately set depending on the size of the tissue of interest, and the like.

Further, the support carrier may have a retentive capacity whereby the cells can maintain their contacting state without being dispersed. As used herein, the "contacting state" is preferably a closely-packed (high density) state which ensures the cell-cell interaction within each cell mass and between the cell masses.

A high density state means a density almost equivalent to the density at which a tissue is constructed, for example, in the case of the cell masses, $5 \times 10^7$ to $1 \times 10^9$ cells/ml at the time of cell positioning, preferably $1 \times 10^8$ to $1 \times 10^9$ cells/ml to ensure the cell-cell interaction without impairing the cell activity, and most preferably $2 \times 10^8$ to $8 \times 10^8$ cells/ml. In order to prepare a cell mass having such a cell density, it is preferred to mass and precipitate cells by centrifugation since this conveniently enables achievement of the high density without impairing the cell activity. Such centrifugation may be carried out at a revolution speed equivalent to a centrifugal force of 300 to 1200×g, which will not adversely affect the survival of the cells, and preferably 500 to 1000×g, for 3 to 10 minutes. Centrifugation at lower than 300×g may lead to insufficient precipitation of the cells and the cell density may become low, while centrifugation at higher than 1200×g may cause damage to the cells, and therefore both of these cases are not preferred.

In cases where high density cells are prepared by centrifugation, the centrifugation is normally carried out after preparing a suspension of single cells in a container such as a tube used for cell centrifugation, and the supernatant is removed to the greatest extent possible, leaving the cells as the precipitates. It is preferred that the container such as a tube be siliconized from the viewpoint of complete removal of the supernatant.

In cases where the precipitates are prepared by centrifugation, these may be directly positioned inside the support carrier. Here, the volume of components other than the cells of interest (for example, a culture medium, a buffer solution, the support carrier or the like) is preferably not more than the volume of the cells, and most preferably, components other than the cells of interest are not contained. In such a high density cell mass, cells are in close contact with each other and the cell-cell interaction may be effectively exerted.

In cases where the cells are used in a tissue state, it is preferred to remove components other than the cells of interest, such as connective tissues, by performing an enzyme treatment or the like. In cases where there are many components other than the cells of interest, for example, in cases where the volume of the other components is not less than that of the cells, the cell-cell interaction may not be sufficiently exerted, which is not preferred.

The closer the contact between the first cell mass and the second cell mass, the better, and it is especially preferred that the second cell mass be positioned such that it presses against the first cell mass. Further, wrapping around the first cell mass and the second cell mass with a solid which does not inhibit a culture medium or oxygen permeation is also effective in making the contact between the cell masses closer. It is also preferred to add a high-density cell suspension to a solution having a different viscosity to position the cell suspension therein, followed by solidification of the solution as is, since this may conveniently achieve maintenance of contacting of the cell. Here, in cases where the first cell mass is an mass of single tooth germ mesenchymal cells and the second cell mass is a tooth germ epithelial tissue, it is preferred to position the enamel knot of the tooth germ epithelial tissue in contact with the first cell mass, but the present invention is not limited to this.

In cases where the support carrier is in the form of a gel, solution or the like, the positioning step may be followed by the solidification step, by which the support carrier is solidified. By the solidification step, cells positioned inside the support carrier may be fixed inside the support carrier. For solidification of the support carrier, conditions generally used for solidification of the support carrier may be applied without modification. For example, in cases where a solidifiable compound such as collagen is used for the support carrier, solidification can be achieved under conditions generally applied, for example, by being left to stand at the culture temperature for several minutes to several tens of minutes. By this, bonds between the cells inside the support carrier can be fixed and made robust.

In the culturing step of the production method of the present invention, a first cell mass and a second cell mass are cultured inside the support carrier. In this culturing step, the cell-cell interaction is effectively exerted by the first cell mass and the second cell mass which are in close contact with each other, to reconstruct a tissue, namely, a tooth.

The culturing step may be carried out such that the contacting state between the first cell mass and the second cell mass is maintained by the support carrier, and may be culturing by the support carrier which simply has the first and the second cell masses, or culturing in the presence of other animal cells.

The time period of the culture varies depending on the number of cells positioned in the support carrier and the states of the cell masses, as well as on the conditions under which the culturing step is carried out, and may be generally 1 to 300 days, preferably 1 to 120 days in order to form a tooth having enamel outside and dentin inside, and preferably 1 to 60 days from the viewpoint of providing the tooth quickly. Further, to form a tooth having a periodontal tissue, the time period may be generally 1 to 300 days, preferably 1 to 60 days.

In cases where the culture was performed only with the support carrier, the culture can be performed under normal conditions used for culturing of animal cells. Here, in general, the conditions for culturing of animal cells can be applied without modification, and the above-mentioned conditions can be applied without modification. Further, serum derived from mammals, and various cellular factors which are known to be effective in growth and differentiation of these cells may be added to the culture. Examples of such cellular factors include FGF and BMP.

Further, it is preferred to use organ culture from the viewpoint of gas exchange and nutrient supply for tissues and cell masses. In organ culture, generally, culturing is performed by floating porous membrane on a culture medium suitable for growth of animal cells and placing a cell mass embedded in a support carrier on the membrane. The porous membrane used herein is preferably a membrane having many pores with the diameter of 0.3 to 5 µm, and specific examples thereof include Cell Culture Insert (trade name) and Isopore Filter (trade name).

Performing the culture in the presence of other animal cells is preferred because a tooth having a specific cell arrangement can be formed at an early stage in response to the actions of various cytokines and the like from the animal cells. Such culture in the presence of other animal cells may be performed by culturing ex vivo using isolated cells or cultured cells.

Further, the support carrier having the first and the second cell masses may be transplanted to a living body to carry out culture in vivo. Such culture in vivo is especially preferred since a tooth and/or a periodontal tissue can be formed at an early stage. In this case, the first and the second cell masses are transplanted together with the support carrier into the living body.

Preferred examples of animals which can be used for this application include mammals such as humans, pigs and mice, and the animal is more preferably derived from the same species as that of the tooth germ tissue. In cases where a human tooth germ tissue is transplanted, it is preferred to use a human, or a mammal other than human which was altered to be immunodeficient. In order to develop an organ or tissue of animal cells as normally as possible, examples of a site in a living body suitable for such in vivo growth preferably include subrenal capsule, mesentery (omentum), subcutaneous and oral cavity.

The time period for the growth according to the transplantation varies depending on the size of the explant at the time of the transplantation and the size of the tooth to be developed, and may be typically 3 to 400 days. For example, the time period of subrenal capsule transplantation is preferably 7 to 60 days from the viewpoints of tooth regeneration and the size of the tooth to be developed at the site of the transplantation, although it varies depending on the size of the explant to be transplanted and the size of the tooth to be regenerated.

Ex vivo culture (preculture) may be performed prior to the transplantation to the living body. The preculture is preferred since the bonds between cells and the bond between the first and the second cell masses can be made strong, to make the cell-cell interaction stronger. As a result, the total growth period can be shortened.

The preculture period may be either short or long. A longer period of time, for example, 3 days or more, preferably 7 days or more, is preferred since a tooth bud can be developed from a tooth germ during this period and thus the time period until a tooth is formed after the transplantation can be shortened. For example, in the case of organ culture for transplantation beneath the subrenal capsule, the time period of preculture is preferably 1 to 7 days in order to efficiently regenerate a tooth.

A tooth produced according to the production method of the present invention has a tooth-specific cell arrangement (structure) having dentin inside and enamel outside, and preferably has directionality, that is, has a tip (crown) and a root of a tooth. By having at least such specific cell arrangement, and preferably by having directionality in addition to the cell arrangement, functions of a tooth can be exerted. Therefore, the produced tooth can be widely used as an alternative to a tooth. Particularly when the mesenchymal cells and epithelial cells derived from an autogenous tooth germ are used, problems caused by rejection can be avoided. Generally, it is also possible to avoid problems caused by rejection in cases where the cells are derived from a tooth germ of another person having a matching transplantation antigen.

The teeth produced by the production method of the present invention may be in the form of a set of teeth having a tooth-specific cell arrangement.

Since such a set of teeth is constituted by multiple teeth having a tooth-specific cell arrangement, each tooth can be separated from the set of teeth and used as an explant of a single tooth as described below. As a result, teeth as explants can be efficiently prepared.

To obtain a set of teeth constituted by multiple teeth, it is preferred that both of the first and the second cell mass be constituted by single cells. By this, plural parts containing factors such as an enamel center which controls the number of teeth may be made to exist, so that plural teeth may be easily formed.

The culturing step may be either organ culture or subrenal capsule culture as described above, and, when the obtained tooth is used as an explant, it is preferred to perform organ culture in which there is no contact with other cells of animals and the entire procedure can be processed in vitro.

Further, in the production method of the present invention, the culture period may be extended until a periodontal tissue is formed. By this, it is possible to form, in addition to a tooth itself, a periodontal tissue such as alveolar bone and periodontal membrane, which support and stabilize teeth on the jaw bone. As a result, a practicable tooth can be provided after the transplantation.

To produce a periodontal tissue, the step to isolate the periodontal tissue obtained by the above culture may be carried out after the above culturing step, to obtain only the periodontal tissue. Isolation of the periodontal tissue may be performed according to any method in which the periodontal tissue formed during the culturing step can be separated from a tooth, and examples of such a method include separation with forceps or the like and partial digestion by enzymes.

The tooth and the periodontal tissue obtained according to the present invention may be used as an explant and may also be preferably used in a research for elucidation of the developmental process of a tooth, so that they may be used as an effective research tool for development of tissues related to teeth in the future.

In cases where the tooth or the periodontal tissue obtained is used as an explant, the culturing step according to the production method is preferably performed as organ culture in which there is no contact with other animal cells and the entire procedure can be processed in vitro.

A method for transplantation of a tooth is also included in the present invention. This method for transplantation includes: a step of obtaining the above-described set of teeth; a step of separating each tooth from a complex of teeth; and a step of transplanting the separated tooth while aligning a tooth such that it has the same directionality as other teeth at the site of the transplantation.

In this way, multiple teeth having a specific cell arrangement and directionality can be obtained simultaneously and tooth transplantation can be performed efficiently.

The tooth according to the present invention can also be applied to therapies or treatments of various symptoms accompanying by loss of or damage to teeth, and examples of the symptoms include dental caries, marginal periodontitis (alveolar pyorrhea), loss of teeth by periodontal diseases, tooth breakage or avulsion caused by accidents or the like.

In other words, the therapeutic method of the present invention includes transplanting of the tooth and/or periodontal tissue obtained by the production method of the present invention into the site of tooth loss and/or damage. By this, the above-described symptoms at the site of tooth loss and/or damage can be treated and/or alleviated.

Another therapeutic method of the present invention includes carrying out only the culturing step of the present invention, or carrying out the positioning step and the culturing step at the site of tooth loss and/or damage. In this case, the surrounding tissue at the site of tooth loss and/or damage itself may be applied as a support carrier in addition to the support carriers mentioned above. Thus, due to cytokines or the like from the surrounding tissues in the living body, therapy or the like of the site of the loss and/or damage can be carried out more quickly.

EXAMPLES

Examples of the present invention will now be described, but the present invention is not limited thereto. Further, "%" in Examples is by weight (mass) unless otherwise specified.
(1) Preparation of Amnion-Derived Mesenchymal Cells For evaluation of the tooth-forming potential of human amniotic mesenchymal cells, human amniotic mesenchymal cells were prepared from human amniotic tissue.

From placenta provided after obtaining informed consent, amniotic tissue was physically isolated. An appropriate amount of PBS(−) was added to a 15 cm dish, and the tissue was cut with surgical scissors and washed using tweezers, to remove blood cells from the obtained amniotic tissue. The amniotic tissue after the treatment was transferred to a new dish, washed again with PBS(−), and further cut, followed by being transferred to a 50 ml centrifuge tube containing 25 ml of 0.25% trypsin (manufactured by GIBCO).

First, to remove amnion-derived epithelial cells, enzyme treatments were carried out as follows. Using a shaking incubator, an enzyme treatment (200 rpm, 15 minutes, 37° C.) was carried out, and the amniotic tissue after the treatment was transferred to a new 50 ml centrifuge tube containing 25 ml of 0.25% trypsin (manufactured by GIBCO), followed by an enzyme reaction (400 rpm, 15 minutes, 37° C.). The trypsin treatment was further repeated 3 times (5 times in total) to mainly remove the epithelial cell layer.

Subsequently, to collect amnion-derived mesenchymal cells, an appropriate amount of PBS(−) was added to a 15 mm dish, and the amniotic tissue after the 5th trypsin treatment was transferred thereto and washed, followed by being cut with scissors into a piece with the size of 5 mm×5 mm. The tissue sample after the cutting was subsequently transferred to a 50 ml centrifuge tube containing an enzyme mixture (1 mg/ml collagenase (manufactured by Sigma), 0.1% Dispase II (manufactured by Roche), 0.01% papain (manufactured by Worthington) and 0.01% DNase (manufactured by Sigma) in Hanks' balanced salt solution), and an enzyme reaction (400 rpm, 1 hour, 37° C.) was carried out in a shaking incubator. The cell suspension obtained from the enzyme treatment was filtered by a metal filter, and the resulting filtrate was transferred to a 50 ml centrifuge tube to be subjected to centrifugation (2000 rpm, 10 minutes, room temperature). The supernatant after the centrifugation was discarded, and the pellet was washed 3 times with PBS(−). After filtering by a 40 μm nylon mesh, centrifugation (at 2000 rpm, for 10 minutes, at room temperature) was carried out to obtain amniotic mesenchymal cells.

The amniotic mesenchymal cells were suspended in DMEM/F12 (manufactured by Sigma) supplemented with 10 ng/ml hLIF (manufactured by Sigma), 0.2 mM mercaptoethanol (manufactured by Sigma) and 10% FCS (JRH Biosciences, Lenexa, Kans.), and plated to a 10 cm cell culture dish at a cell density of 1 to 5×10$^5$ cells/ml. Until preparation of a reconstructed tooth germ, the cells were dispersed by trypsin treatment and subcultured, as appropriate.
(2) Preparation of Tooth Germ Epithelial Tissue From an embryo (at the fetal age of 14.5 days) of C57BL/6-TgN(act-EGFP)OsbC14-Y01-FM131 (purchased from RIKEN BioResource Center) which is Green Fluorescence Protein (EGFP) transgenic mouse, a lower incisor tooth germ was removed under the microscope by a conventional method. The lower incisor tooth germ tissue was washed with $Ca^{2+}/Mg^{2+}$-free phosphate buffer (PBS(−)), and treated at room temperature for 12.5 minutes with the enzyme solution which is PBS(−) supplemented with 1.2 U/ml (final concentration) Dispase II (manufactured by Roche)). This was followed by washing with DMEM (manufactured by Sigma) supplemented with 10% FCS (manufactured by JRH) 3 times. Subsequently, a DNase I solution (manufactured by Takara) was added to a final concentration of 70 U/ml to disperse the tooth germ tissue, and the tooth germ epithelial tissue was surgically separated using a 25 G injection needle (manufactured by Terumo).
(3) Preparation of Reconstructed Tooth Germ Preparation of a reconstructed tooth germ was carried out using the above-prepared tooth germ epithelial tissue and human amniotic mesenchymal cells.

Human amniotic mesenchymal cells were collected from the dish by trypsin treatment. In a 1.5 ml microtube (manufactured by Eppendorf) to which silicone grease was applied, human amniotic mesenchymal cells suspended in DMEM (manufactured by Sigma) supplemented with 10% FCS (manufactured by JRH) were added, and the cells were collected by centrifugation as precipitates. The supernatant of the culture medium after the centrifugation was removed as much as possible, and centrifugation was carried out again, followed by complete removal of the culture medium remaining around the precipitates of the cells under a stereoscopic microscope using GELoader Tip 0.5-20 μl (manufactured by eppendorf), to prepare human amniotic mesenchymal cells to be used for preparation of a reconstructed tooth germ.

To a petri dish to which silicone grease was applied, 30 μl of 2 mg/ml Cellmatrix type I-A (manufactured by Nitta Gelatin Inc.) was added dropwise to prepare a collagen gel droplet. To this solution, 0.2 to 0.3 μl of the above-described amniotic mesenchymal cells were applied using a 0.1-10 μl pipette tip (manufactured by Quality Scientific plastics) to prepare a cell aggregate. Subsequently, using a 10 μl pipette tip, the tooth germ epithelial tissue was applied to the same gel droplet, and, using a tungsten needle, the surface of the separated tooth germ epithelial tissue which was originally in contact with a mesenchymal tissue was brought into close contact with the cell aggregate of the human amniotic mesenchymal cells. Thereafter, by solidifying the gel droplet, the bonds between the tooth germ epithelial tissue and the human amniotic mesenchymal cells were made stronger, to prepare a high-density reconstructed tooth germ.

This will now be described referring to FIG. 1. In FIG. 1, the number 10 represents the gel droplet (support carrier), the number 12 represents the cell aggregate (the first cell mass), the number 14 represents the cell aggregate (the second cell mass) and the number 16 represents the pipette tip.

Figure 1B:
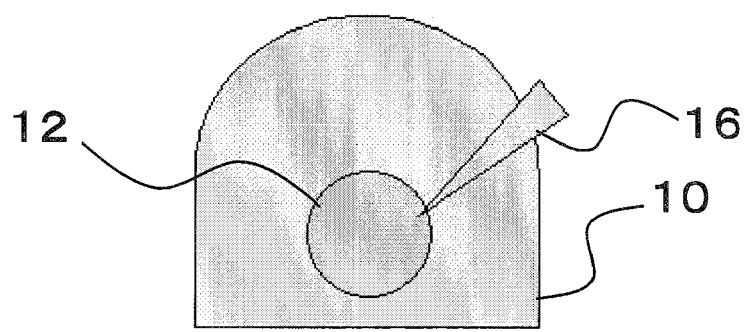
FIG. 1B is a schematic conceptual view showing the procedure according to Examples of the present invention for reconstruction of a tooth germ using mesenchymal cells and epithelial cells derived from a tooth germ, and showing the state of positioning of a first cell mass in a gel drop.
Figure 1C:
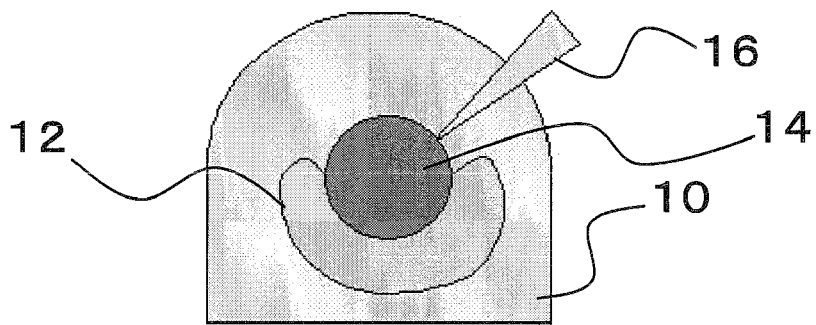
FIG. 1C is a schematic conceptual view showing the procedure according to Examples of the present invention for reconstruction of a tooth germ using mesenchymal cells and epithelial cells derived from a tooth germ, and showing the state of positioning of a second cell mass in a gel drop.
Figure 1D:
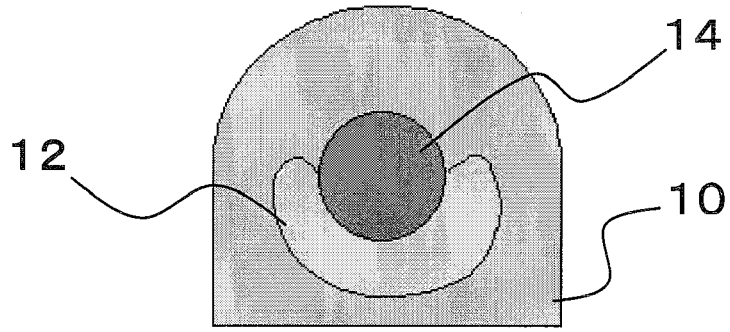
FIG. 1D is a schematic conceptual view showing the procedure according to Examples of the present invention for reconstruction of a tooth germ using mesenchymal cells and epithelial cells derived from a tooth germ, and shows the solidified state of a gel drop in which the first cell mass and the second cell mass are positioned.

The cell aggregate 12 which was previously positioned in the gel droplet 10 (see FIG. 1(A)) with the pipette tip 16 constitutes a sphere in the gel droplet 10 (see FIG. 1(B)). Subsequently, by pressing the other cell aggregate 14 thereinto, the spherical cell aggregate 12 is crushed to wrap the other cell aggregate 14 (see FIG. 1(C)). Thereafter, by solidifying the gel droplet 10, bonds between the cells become strong (see FIG. 1(D)).

(4) Organ Culture of Reconstructed Tooth Germ

The high-density reconstructed tooth germ prepared in the gel was left to stand in a $CO_2$ incubator for 10 minutes to solidify Cellmatrix type I-A (Nitta Gelatin). A culture vessel was prepared such that DMEM (manufactured by Sigma) supplemented with 10% by volume FCS (manufactured by JRH), 0.1 mg/ml L-ascorbic acid (manufactured by Sigma) and 2 mM L-glutamine (manufactured by GIBCO) is in contact with Cell Culture Inserts (PET membrane having a pore size of 0.4 μm; manufactured by BD). The reconstructed tooth germ was transferred, together with the surrounding gel which is the support carrier, onto the membrane of Cell Culture Inserts in the culture vessel, to carry out organ culture.

Usually, in cases where development of a tooth was analyzed by organ culture, 14 days of culture was carried out. When organ culture was carried out, a reconstructed tooth germ was fixed with 4% paraformaldehyde-phosphate buffer for 6 hours, followed by 24 hours of neutral decalcification using 4.5% EDTA solution (pH 7.4). Thereafter, paraffin embedding was carried out according to a conventional method to prepare 10 μm sections. For a histological analysis, hematoxylin eosin staining (HE staining) was carried out according to a conventional method.

In cases where a tooth germ derived from C57BL/6-TgN (act-EGFP)OsbC14-Y01-FM131 mouse was used, the tooth germ was subjected to neutral decalcification and treated with 12.5% sucrose (manufactured by Wako) for 12 hours and with 25% sucrose (manufactured by Wako) for 12 hours, followed by being embedded in OCT compound (manufactured by Miles Inc.) to prepare sections with the size of 10 μm using a cryostat (manufactured by Leica), for observation under a fluorescence microscope (manufactured by ZEISS). Histological analysis was carried out by hematoxylin eosin staining (HE staining) according to a conventional method.

(5) Evaluation by Organ Culture

Figure 2:
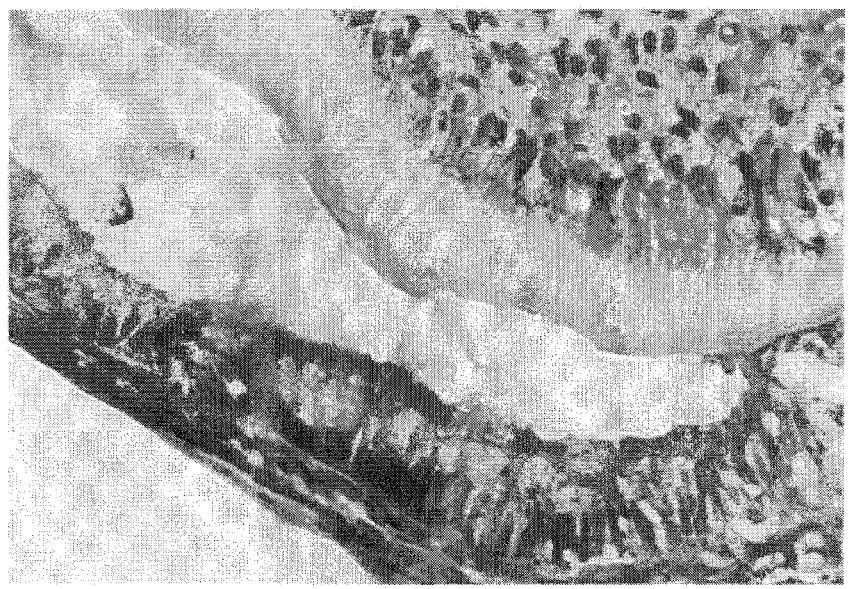
FIG. 2 is an HE-stained image of the reconstructed tooth germ of the example of the present invention after organ culture. The bar in the figure represents 25 μm.

As shown in FIG. 2, a regenerated tooth was formed by organ culture of the reconstructed tooth germ obtained as described above. This regenerated tooth had, from the outside, ameloblasts, enamel, dentin and odontoblasts, and dental pulp cells at the center. This cell arrangement is the same as that of a normal tooth.

By these, according to this Example, it became clear that culturing of human amniotic mesenchymal cells and a tooth germ epithelial tissue at a high density under compartmentalization enables formation of a tooth having the specific tissue structure, through an effective interaction between the mesenchymal cells and the epithelial tissue.

Thereafter, the origins of the cells constituting the formed tooth were confirmed using a differential interference microscope and a fluorescence microscope.

Figure 3:
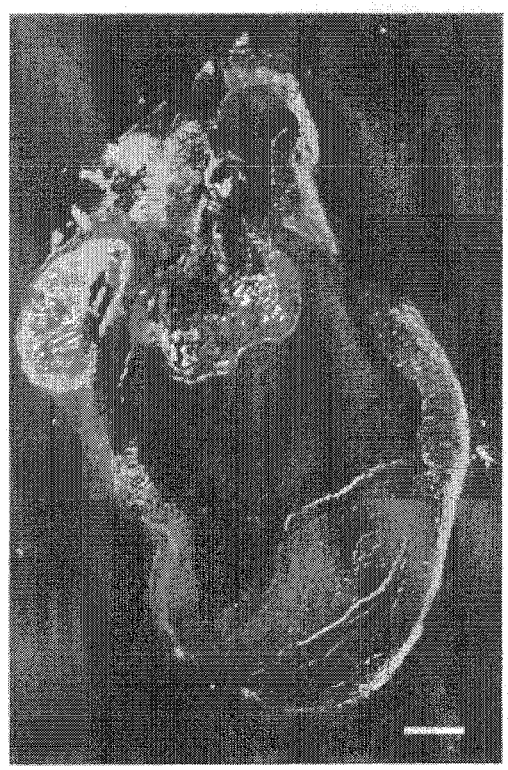
FIG. 3 is a diagram in which a fluorescence micrograph and a differential interference micrograph after organ culture of the reconstructed tooth germ of the example of the present invention are superimposed. The bar in the figure represents 100 μm.

According to observation under a differential interference microscope, the tissue structure specific to a tooth, that is, from the outside, ameloblasts, enamel, dentin and odontoblasts, and dental pulp cells at the center, could be confirmed as in the case of the organ culture of a tooth germ. Further, as shown in FIG. 3, it was revealed that, according to observation of GFP under a fluorescence microscope, the ameloblasts located outside the enamel were GFP-positive (bright parts in FIG. 3) while the odontoblasts and dental pulp cells located inside the dentin were GFP-negative (dark parts in FIG. 3).

These results indicate that the ameloblasts located outside the enamel are cells derived from epithelial cells, and the odontoblasts and dental pulp cells located inside the dentin are derived from amniotic mesenchymal cells.

As a result, according to the present invention, compartmentalized culturing of amnion-derived mesenchymal cells and a tooth germ-derived epithelial tissue enables formation of a tooth having a specific cell arrangement. Further, it is clear that amnion-derived mesenchymal cells are useful for formation of a tooth.

The disclosure of Japanese Patent Application No. 2007-49128 is hereby incorporated by reference in its entirety.

All the literatures, patent applications and technical standards described in the present specification are hereby incorporated by reference to the same extent as in cases where each literature, patent application or technical standard is concretely and individually described to be incorporated by reference.

The invention claimed is:

1. A method for producing a tooth, the method comprising:
   isolating or obtaining mesenchymal cells from an amnion and preparing a first cell mass consisting essentially of the mesenchymal cells;
   isolating or obtaining epithelial cells from a tooth germ and preparing a second cell mass consisting essentially of the epithelial cells;
   positioning said first and second cell masses in a support carrier capable of promoting tooth formation, wherein the first and second cell masses are not mixed but placed in close contact with each other within the support carrier; and
   culturing the first and second cell masses in the support carrier for an amount of time sufficient to produce a tooth.

2. The method according to claim 1, wherein said isolating or obtaining mesenchymal cells from an amnion comprises isolating or obtaining mesenchymal cells from an amniotic compact layer of said anion.

3. The method according to claim 1, wherein said first cell mass is composed of single cells.

4. The method according to claim 1, wherein said first cell mass and second cell mass are both composed of single cells.

5. The method according to claim 1, wherein said support carrier is at least one selected from the group consisting of collagen, fibrin, laminin, an extracellular matrix mixture, polyglycolic acid (PGA), polylactic acid (PLA), and lactic acid/glycolic acid copolymer (PLGA).

6. The method according to claim 1, further comprising continuing said culturing step until a tooth and periodontal tissue are formed.

7. The method according to claim 1, wherein multiple teeth are formed simultaneously after said culturing, thereby resulting in a complex of teeth.

8. A method for transplanting a tooth, the method comprising:
    obtaining a complex of teeth prepared by the method according to claim 7;
    separating each tooth from the complex of teeth to produce a separated tooth; and
    transplanting said separated tooth into a transplantation site comprising other teeth and aligning said separated tooth with said other teeth present at said transplantation site.

9. A method for treating a lost tooth or replacing a damaged tooth in a subject, the method comprising:
    transplanting a tooth and/or periodontal tissue obtained by the method according to claim 6 into a site of a lost tooth or an extracted, damaged tooth in a subject.

10. The method according to claim 1, wherein the support carrier is a gel support carrier and wherein said first cell mass is positioned in the gel support carrier before positioning said second cell mass in the gel support carrier.

11. The method according to claim 10, wherein the gel support carrier is a collagen gel support carrier.

12. The method according to claim 10, further comprising:
    solidifying the gel after the second cell mass is brought into close contact with the first cell mass.

\* \* \* \* \*